United States Patent [19]

Yamada

[11] Patent Number: 4,506,085
[45] Date of Patent: Mar. 19, 1985

[54] β-AMINOACID DERIVATIVES AND PROCESS FOR PRODUCTION THEREOF

[75] Inventor: Yasuji Yamada, Hachioji, Japan

[73] Assignee: Sanraku-Ocean Co., Ltd., Tokyo, Japan

[21] Appl. No.: 586,143

[22] Filed: Mar. 5, 1984

[30] Foreign Application Priority Data

Mar. 9, 1983 [JP] Japan .................................. 58-37252

[51] Int. Cl.³ .......................................... C07D 317/00
[52] U.S. Cl. .................... 549/451; 549/342; 549/454
[58] Field of Search .............................. 549/451, 342

[56] References Cited

U.S. PATENT DOCUMENTS 4,424,370  1/1984  Kleeman et al. .................... 549/452

OTHER PUBLICATIONS

Tetrahedron Letters, vol. 21, pp. 2783–2786, (1980).
Tetrahedron Letters, vol. 22, pp. 913–916, (1981).
Chem. Pharm. Bull., 30(5), 1929–1931, (1982).

Primary Examiner—Ethel G. Love
Attorney, Agent, or Firm—Wenderoth, Lind & Ponack

[57] ABSTRACT

A compound represented by the formula

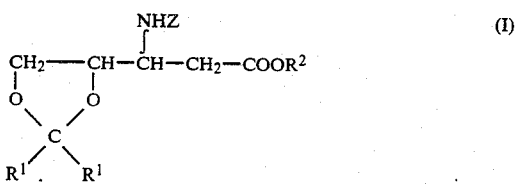

wherein $R^1$ represents a lower alkyl group, a phenyl group or a benzyl group, or the two $R^1$ groups together represent a group of the formula $-CH_2-_n$ in which n is an integer of 4 to 7; $R^2$ represents a hydrogen atom, an alkyl group, or a substituted or unsubstituted aralkyl group; and Z represents a hydrogen atom, a lower alkyl group or a substituted or unsubstituted benzyl group;

and a process for production thereof. The compounds of this invention are useful as intermediates for the synthesis of various biologically active substances, such as various antibiotics, particularly β-lactam antibiotic derivatives, thienamycin, antibiotic PS-5 and their analogous substances.

4 Claims, No Drawings

β-AMINOACID DERIVATIVES AND PROCESS FOR PRODUCTION THEREOF

This invention relates to novel β-amino acid derivatives. More specifically, it relates to compounds represented by the following formula

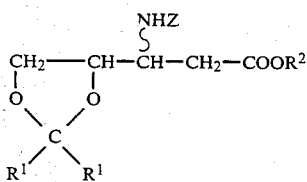

(I)

wherein $R^1$ represents a lower alkyl group, a phenyl group or a benzyl group, or the two $R^1$ groups together represent a group of the formula —$CH_2$—$_n$ in which n is an integer of 4 to 7; $R^2$ represents a hydrogen atom, an alkyl group, or a substituted or unsubstituted aralkyl group; and Z represents a hydrogen atom, a lower alkyl group or a substituted or unsubstituted benzyl group,
and to a process for producing these compounds.

In the present specification and claims, the term "lower" used to qualify a group or compound means that the group or compound so qualified has not more than 6, preferably not more than 4, carbon atoms.

In formula (I), the "lower alkyl group" represented by $R^1$ and/or Z may be linear or branched, and includes, for example, methyl, ethyl, n-propyl, isopropyl, n-butyl, isobutyl, sec-butyl and n-pentyl. Methyl and ethyl groups are preferred.

The "alkyl group" represented by the ester residue $R^2$ may be linear or branched, and may generally contain not more than 10 carbon atoms, preferably not more than 6 carbon toms. Examples of the "alkyl group" include methyl, ethyl, n-propyl, isopropyl, n-butyl, isobutyl, sec-butyl, tert-butyl, n-pentyl, isopentyl, n-hexyl, isohexyl and n-heptyl. Of these, lower alkyl groups are preferred.

The "substituted or unsubstituted aralkyl group" represented by the ester residue $R^2$ includes, for example, benzyl, phenethyl, benzhydryl, trityl and o- or p-nitrobenzyl groups.

The "substituted benzyl group" represented by the amino protecting group Z may be a benzyl group which is substituted by 1 to 3 substituents selected, for example, from lower alkyl groups, lower alkoxy groups, halogen atoms, nitro groups, and hydroxyl groups. Suitable substituted benzyl groups are those having electron donating substituents (such as lower alkyl or alkoxy groups), for example p-methoxybenzyl, p-methylbenzyl, o,p-dimethoxybenzyl, o,p-dimethylbenzyl , and o-ethoxybenzyl groups.

A preferred group of the compounds of formula (I) includes those represented by the following formula

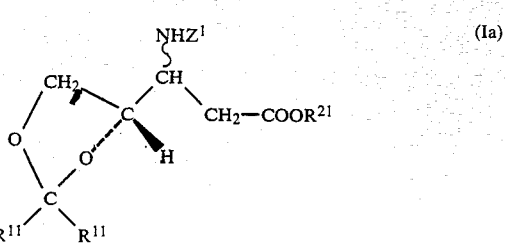

wherein $R^{11}$ represents a methyl or ethyl group or the two $R^{11}$ groups together represent —$CH_2$—$_5$; $R^{21}$ represents a hydrogen atom or a lower alkyl group; and $Z^1$ represents a group of the formula

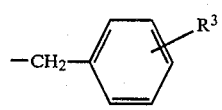

in which $R^3$ represents a lower alkyl group, particularly a methyl group, or a lower alkoxy group, particularly a methoxy group.

In formula (Ia), the asymmetric carbon atom at the β-position can take either an (R)-configuration or an (S)-configuration, the former being particularly preferred.

Typical examples of the compounds of formula (I) provided by this invention are listed below.

(1) 3R, 4R-4,5-O-isopropylidene-3-(benzylamino)-pentanoic acid,
(2) 3S, 4S-4,5-O-isopropylidene-3-(benzylamino)pentanoic acid,
(3) 3R, 4S-4,5-O-isopentylidene-3-(benzylamino)pentanoic acid,
(4) 3S, 4S-4,5-O-isopentylidene-3-(benzylamino)pentanoic acid,
(5) 3R, 4S-4,5-O-cyclohexylidene-3-(benzylamino)-pentanoic acid,
(6) 3S, 4S-4,5-O-cyclohexylidene-3-(benzylamino)-pentanoic acid,
(7) 3R, 4S-O-isopropylidene-3-(p-methoxybenzyl)-pentanoic acid,
(8) 3S, 4S-O-isopropylidene-3-(p-methoxybenzyl)-pentanoic acid,
(9) 3R, 4S-O-isopropylidene-3-(p-methylbenzyl)pentanoic acid,
(10) 3S, 4S-O-isopropylidene-3-(p-methylbenzyl)pentanoic acid,
(11) 3R, 4S-O-cyclohexylidene-3-(p-methoxybenzyl)-pentanoic acid,
(12) 3S, 4S-O-cyclohexylidene-3-(p-methoxybenzyl)-pentanoic acid,
(13) 3R, 4S-O-cyclohexylidene-3-(p-methylbenzyl)-pentanoic acid,
(14) 3R, 4S-O-isopropylidene-3-(amino)pentanoic acid,
(15) 3S, 4S-O-isopropylidene-3-(amino)pentanoic acid,
(16) 3R, 4S-O-isopropylidene-3-(methylamino)pentanoic acid,
(17) 3R, 4S-O-isopropylidene-3-(isopropylamino)-pentanoic acid, and
(18) 3R, 4S-O-isopropylidene-3-(ethylamino)pentanoic acid.

The methyl, ethyl, benzyl and p-nitrobenzyl esters of the compounds (1) to (18) above may also be cited as examples.

According to this invention, the compound of formula (I) can be produced by subjecting a compound represented by the following formula

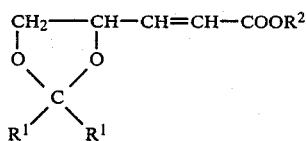  (II)

wherein R¹ and R² are as defined above, and an amine represented by the following formula

ZNH₂  (III)

wherein Z is as defined above, to the Michael type of addition reaction.

A compound (4S-form) of formula (II) which is derived from D-mannitol can include the following two geometric isomers [see J. American Chemical Society, 43, 4438 (1978)].

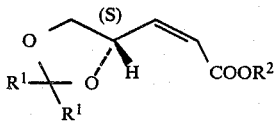

(II-1)

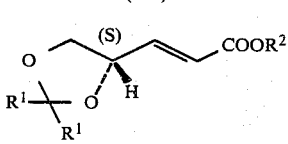

(II-2)

In the process of this invention, either of these isomers or a mixture of these isomers can be used. By using L-mannitol as a material for preparation of the compound of formula (II), (4R) isomers which are epimers of the compounds represented by the above formulae (II-1) and (II-2) are obtained. These (4R) isomers can likewise be used in the present invention.

The Michael's addition reaction between the compound of formula (II) and the amine of formula (III) can be carried out in a manner known per se. For example, it can be carried out by reacting the compound of formula (II) with the amine of formula (III) in the absence of solvent or in the presence of a suitable inert solvent such as ethanol, methylene chloride, diethyl ether, N,N-dimethylformamide (DMF), benzene, toluene, or tetrahydrofuran (THF) at a relatively low temperature of, for example, generally about −80° C. to about 35° C., preferably not more than about 10° C. As the reaction temperature is lower, the diastereomeric selectivity for the compound of formula (1) [(R) form] of the β-(R)-configuration becomes higher. For example, when the reaction is carried out at a temperature of not more than about −50° C., the compound of the (R) form is formed in a selectivity of nearly 100%.

The proportion of the amine of formula (III) relative to the compound of formula (II) is not particularly restricted. Generally, the suitable proportion of the amine of formula (III) is at least 1 mole, preferably at least 3 moles, per mole of the compound of formula (II). Alternatively, by using a large excess of the amine (III), it may be caused to serve concurrently as a solvent, and this results in an increase in the selectivity of the reaction.

As a result, the desired compound of formula (I) is obtained in a high yield. When a compound of formula (II) (4S-isomer) derived from D-mannitol is used as the starting material, the compound of formula (I) may be obtained in the form of a diastereomer, i.e., a mixture of two isomers of the following formulae depending upon the reaction conditions.

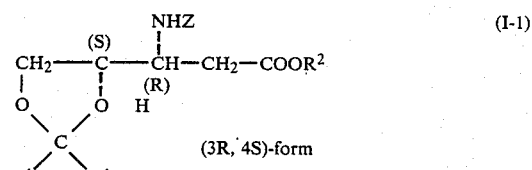

(3R, 4S)-form

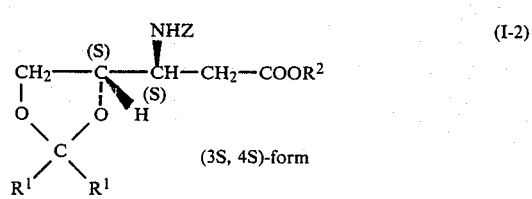

(3S, 4S)-form

The diastereomer can be separated into the (3R, 4S)-isomer and the (3S, 4S)-isomer by subjecting it to silica gel thin-layer chromatography, column chromatography or high-performance liquid chromatography known per se.

By using a compound of formula (II) (i.e., 4R-isomer) derived from L-mannitol, a mixture of the following two isomers (i.e., diastereomer) is obtained.

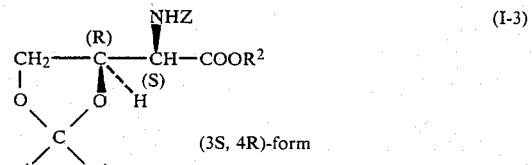

(3S, 4R)-form and

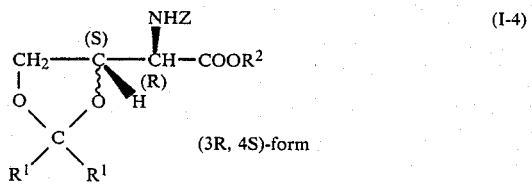

(3R, 4S)-form

The diastereomer can be separated in the same way as above.

It should be understood therefore that the formula (I) includes the (3R, 4S)-form, (3S, 4S)-form, (3R, 4R)-form, (3S, 4R)-form, and mixtures of these four forms.

The compounds of formula (I) provided by this invention are useful as intermediates for the synthesis of various biologically active substances, such as various antibiotics, particularly β-lactam antibiotic derivatives, thienamycin, antibiotic PS-5 and their analogous substances. For example, a compound of formula (I-1) in which R¹ and R² are methyl groups and Z is a benzyl group (Bn) can be converted to thienamycin, known as an antibacterial agent, through the following reaction routes. For details of the reactions, reference may be had to Referential Examples 2 and 3 given hereinbelow.
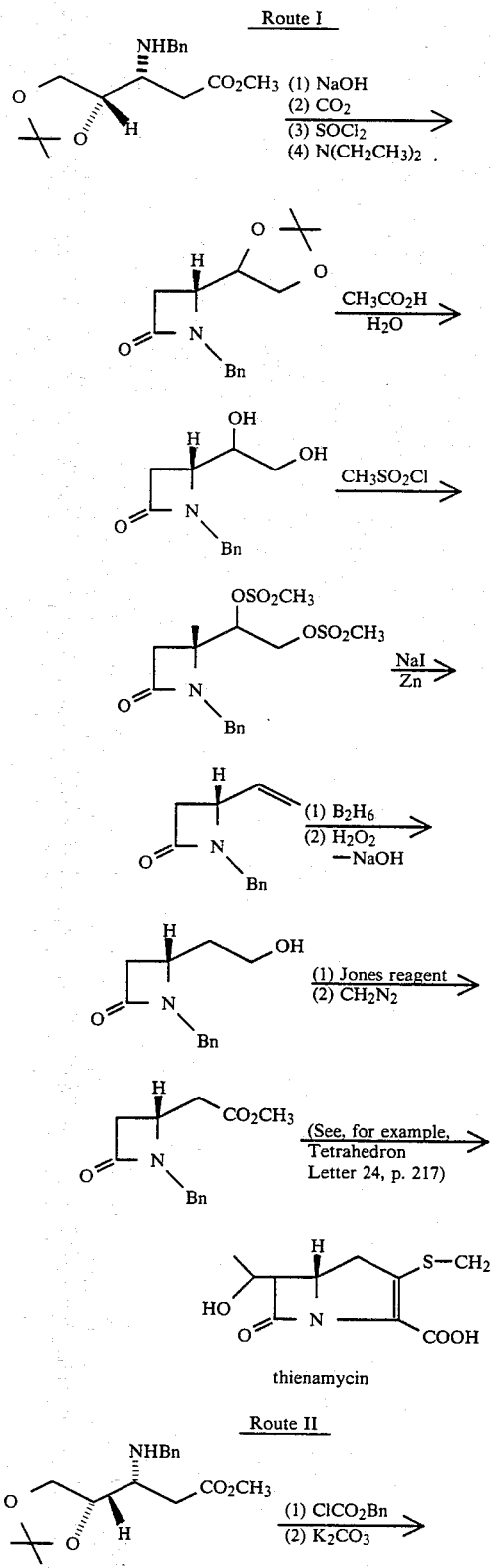
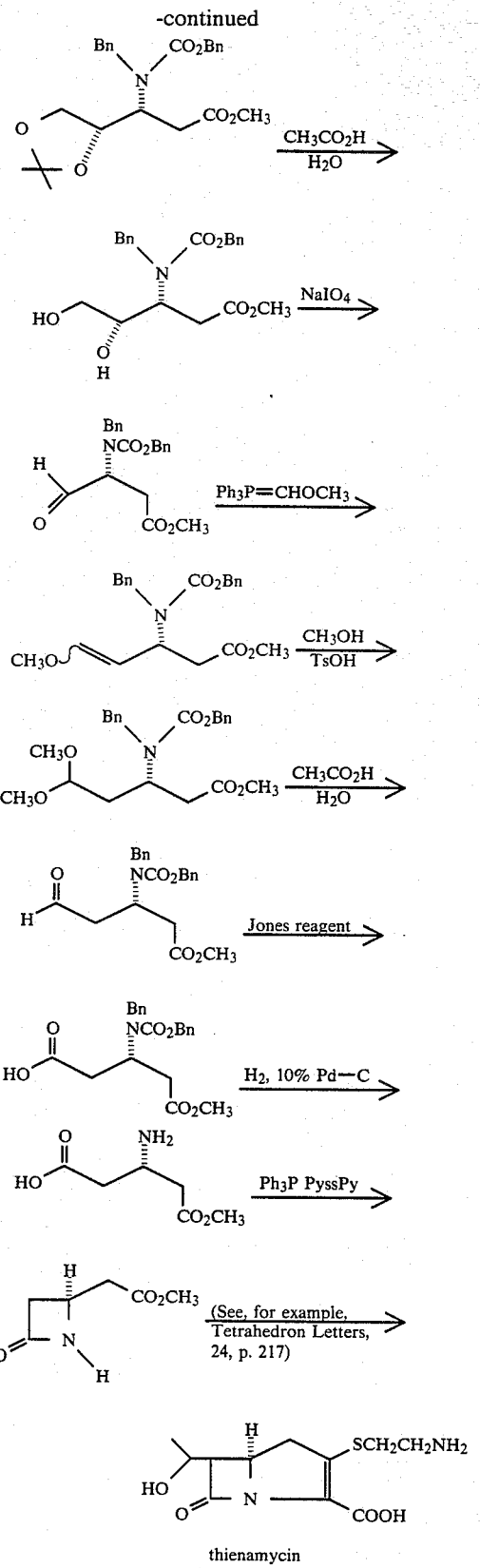
In the above reaction schmes, Bn represents a benzyl group; Ph, a phenyl group; py, a pyridinyl group; and Ts,

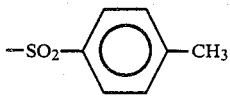

(the same abbreviations may be used hereinafter).

By using the (S)-form compound as the starting material, thienamycin of the 5R-form (natural form) can be produced in accordance with Route I, and thienamycin of the 5S-form (non-natural form), in accordance with Route II.

The following Examples and Referential Examples illustrate the present invention more specifically.

EXAMPLE 1

Production of methyl (3R or 3S, 4S)-4,5-O-isopropylidene-3-(benzylamino)pentanoate:

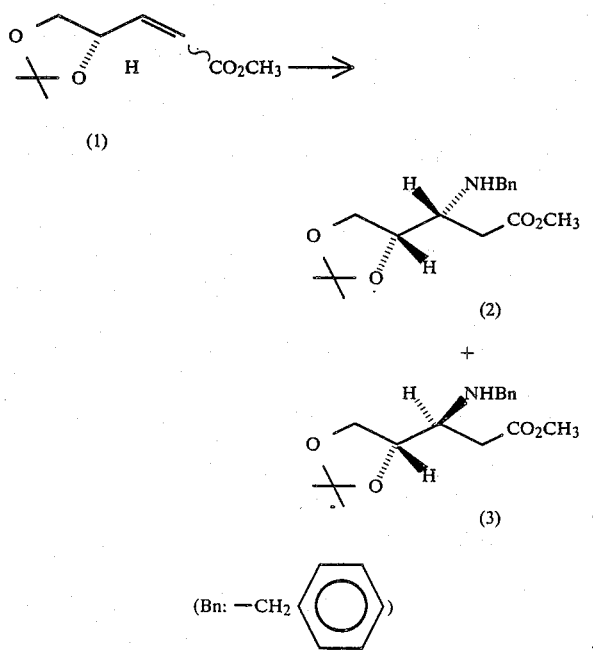

(Bn: —CH₂—⟨○⟩)

Dry tetrahydrofuran (10 ml) was added to 2 g (11 mmoles) of the α,β-unsaturated ester (1) to dissolve the ester (1), and then 3.6 ml (33 moles) of benzylamine was added. The mixture was stirred at 0° C. for 6 hours. After the reaction, the temperature was returned to room temperature (20° C.), and tetrahydrofuran was evaporated under reduced pressure. The residue was chromatographed on a silica gel column using a mixture of ethyl acetate and n-hexane as an eluent to give 3.2 g (yield 93%) in total of the compounds (2) and (3) (4:1). The analytical data were as follows:

Compound (2)

Boiling point: 135°-138° C. (2 mmHg)
IR $\nu_{max}^{CHCl_3}$ cm$^{-1}$: 3330, 1720, 1600.
$^1$H-NMR (270 MHz) $\delta_{ppm}^{CDCl_3}$: 1.34 (3H, s, —CH₃), 1.40 (3H, s, —CH₃), 1.67 (1H, —NH, vanished in D₂O), 2.54 (2H, m, —CH₂CO—), 3.13 (1H, m, —CHNH—), 3.68 (3H, s, —CO₂CH₃), 3.84 (2H, d, J=5 Hz, —CH₂C₆H₅), 3.88 (2H, m, —OCH₂—), 4.24 (1H, m, —CH<), 7.31 (5H, s, —C₆H₅).
MS m/z: 294 (M+1).

High resolution MS: $C_{16}H_{23}NO_4$; Calcd. 293.1625, Found 293.1597.
$[\alpha]_D^{20}$: —8.0 (C 1.3, ethanol).

Compound (3)

IR $\nu_{max}^{CHCl_3}$ cm$^{-1}$: 3330, 1720, 1600.
$^1$H-NMR (270 MHz) $\delta_{ppm}^{CDCl_3}$: 1.34 (3H, s, —CH₃), 1.40 (3H, s, —CH₃), 1.67 (1H, —NH, vanished in D₂O), 2.54 (2H, m, —CH₂CO—), 3.08 (1H, m, —CHNH—), 3.68 (3H, s, —CO₂CH₃), 3.84 (2H, d, J=5 Hz, —CH₂C₆H₅), 3.88 (2H, m, —O—CH₂—), 4.14 (1H, m, —CH<), 7.31 (5H, s, —C₆H₅).
MS m/z: 294 (M+1).
$[\alpha]_D$+14.6° (C 1.0, ethanol).

EXAMPLE 2

Selective production of methyl (3R, 4S)-4,5-O-isopropylidene-3-(benzylamino)pentanoate The α,β-unsaturated ester (1) (186 mg; 1.00 mmole) was treated with 214 mg (2.00 mmoles) of benzylamine, and the mixture was stirred in an argon atmosphere at —50° C. for 50 hours. After the reaction, the reaction mixture was chromatographed on a silica gel column using acetic acid/hexane (2/5) as an eluent to give 215 mg (yield 85%) of the title compound having the physicochemical properties shown in Example 1. No compound (3) was observed in the reaction mixture.

REFERENTIAL EXAMPLE 1

Production of methyl (4S)-4,5-O-isopropylidene-2-pentanoate (an example of the α,β-unsaturated ester used in the invention)

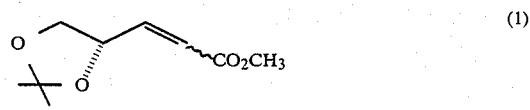

(1)

Step A (production of 1,2,5,6-O-diisopropylidene-D-mannitol)

Anhydrous zinc chloride (270 g; 1.98 moles) was dissolved in 1350 ml of anhydrous acetone, and 170 g (933 mmoles) of D-mannitol was added to the solution. The mixture was stirred at room temperature (25° C.) for 2 hours. Immediately after the reaction, the organic layer was added to an aqueous solution of potassium carbonate, and the mixture was stirred for 1 hour. Subsequently, 1350 ml of diethyl ether was added to the mixture, and the mixture was stirred at room temperature for 30 minutes. The acetone/diethyl ether layer was taken out, and dried over anhydrous potassium carbonate. The solvents were evaporated. The resulting crude crystals were recrystallized from di-n-butyl ether to give 100 g (41%) of 1,2,5,6-O-diisopropylidene-D-mannitol was obtained.

Melting point: 117°-119° C.
IR $\nu_{max}^{KBr}$ cm$^{-1}$: 3300.
$^1$H-NMR $\delta_{ppm}^{CDCl_3}$: 1.29 (6H, s, —CH₃), 1.31 (6H, s, —CH₃), 2.67 (2H, brs, —OH, vanished in D₂O), 4.0 (8H, m).

By subjecting various carbonyl compounds in place of acetone to the above reaction, the corresponding alkylidene compounds can be obtained.

Step B (production of 2,3-O-isopropylidene-1-propanal)

Thirty grams (116 mmoles) of 1,2,5,6-O-diisopropylidene-D-mannitol was dissolved in 135 ml of methanol, and at 0° C., 40 ml of a 5% aqueous solution of sodium hydrogen carbonate and 25 g (116 mmoles) of sodium metaperiodate were added, and the mixture was stirred for 1 hour. The reaction mixture was filtered, and the filtrate was extracted three times with 500 ml of dichloromethane. The extracts were washed with a saturated aqueous solution of sodium chloride, and dried over anhydrous sodium sulfate. The solvent was evaporated, and the residue was distilled under reduced pressure to give 157 g (52%) of 2,3-O-isopropylidene-1-propanal.

Boiling point: 39°–42° C. (11 mmHg).

IR$\nu_{max}^{CHCl_3}$ cm$^{-1}$: 1730.

$^1$H-NMR (90 MHz) $\delta_{ppm}^{CDCl_3}$: 1.48 (3H, s, —CH$_3$), 1.50 (3H, s, —CH$_3$), 4.15 (3H, m, —CH$_2$CH<), 9.71 (1H, d, J=2 Hz, —CHO).

Step C (production of methyl (4S)-4,5-O-isopropylidene-2-pentanoate)

7.2 g (56 mmoles) of 2,3-O-isopropylidene-1-propanal was dissolved in 200 ml of methanol, and at 0° C., the solution was added dropwise over 30 minutes to 100 ml of a methanol solution of 22 g (66 mmoles) of Ph$_3$P=CHCO$_2$CH$_3$. The mixture was stirred at 0° C. for 12 hours. After the reaction, the solvent was evaporated, and 200 ml of a 50% aqueous solution of methanol was added. The mixture was extracted with 150 ml of n-hexane four times. The extracts were washed with a saturated aqueous solution of sodium chloride, and dried over anhydrous sodium sulfate. The solvent was evaporated, and the residue was distilled under reduced pressure to give the α,β-unsaturated ester (87.5%) of (Z)-form and its geometric isomer (12.5%) as colorless oils. 7.92 g (77.4%). The analytical data were as follows:

Z-form

Boiling point: 49°–52° C. (1 mmHg).

IR $\nu_{max}^{CHCl_3}$ cm$^{-1}$: 1720.

$^1$H-NMR (90 MHz) $\delta_{ppm}^{CDCl_3}$: 1.43 (3H, s, —CH$_3$), 1.47 (3H, s, —CH$_3$), 3.64 (1H, dd, J=7.2, 8.7 Hz, —OCH$_2$—), 3.75 (3H, s, —CO$_2$CH$_3$), 4.42 (1H, dd, J=7.2, 8.7 Hz, —OCH$_2$—), 5.53 (1H, dq, J=1.5, 7.2 Hz, —CH<), 5.85 (1H, dd, J=1.5, 12 Hz, —CH=CHCO—), 6.40 (1H, dd, J=7.2, 12 Hz, —CH=CHCO—).

E-form

Boiling point: 58°–62° C. (1 mmHg).

IR $\nu_{max}^{CHCl_3}$ cm$^{-1}$: 1720.

$^1$H-NMR (90 MHz) $\delta_{ppm}^{CDCl_3}$: 1.41 (3H, s, —CH$_3$), 1.46 (3H, s, —CH$_3$), 3.70 (1H, dd, J=6.6, 8.4 Hz, —OCH$_2$—), 3.77 (3H, s, —CO$_2$CH$_3$), 4.21 (1H, dd, J=6.6, 8.4 Hz, —OCH$_2$—), 4.71 (1H, dq, J=1.5, 6.6 Hz, —CH<), 6.15 (1H, dd, J=1.5, 15 Hz, —CH=CHCO—), 6.94 (1H, dd, J=6.6, 15 Hz, —CH=CHCO—).

REFERENTIAL EXAMPLE 2

Production of (4R)-1-benzyl-4-(methoxycarbonylmethyl)-2-azetidinone

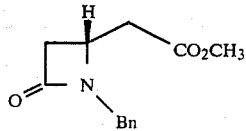

Step A [production of (4R)-1-benzyl-4-(1,2-O-isopropylideneethyl)-2-azetidinone]

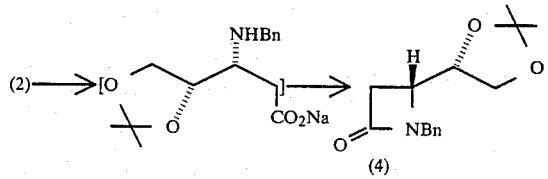

Fifty milliliters of a 0.01N ethanol solution of sodium hydroxide was added to 1 g (3.4 mmoles) of the compound (2), and the resulting solution was stirred at room temperature (20° C.) for 15 hours. After the reaction, ethanol was evaporated under reduced pressure. Without isolating a carboxylic acid compound derived from the compound (2), 10 ml of distilled water was added to the residue. Dry ice was added little by little to adjust the pH of the solution to 7. Water was evaporated under reduced pressure, and the residue was dissolved in 30 ml of dry benzene. Under an argon stream, 0.75 ml (10 mmoles) of thionyl chloride was added, and the mixture was stirred at 80° C. for 1 hour. After the reaction, the temperature was returned to room temperature (20° C.), and benzene was evaporated under reduced pressure. The residue was dissolved in 30 ml of dry benzene, and 0.62 ml (4.4 mmoles) of triethylamine was gradually added dropwise to the solution.

The mixture was stirred under an argon stream at room temperature (20° C.) for 12 hours. Benzene was evaporated under reduced pressure, and the residue was dissolved in a mixture of diethyl ether and dichloromethane (2:1). The solution was filtered, and the filtrate was evaporated under reduced pressure. The resulting oily product was chromatographed on a silica gel column using a mixture of diethyl ether and dichloromethane as an eluent. Fractions containing the compound (4) were combined, and distilled under reduced pressure to give 412 mg (46.3%) of the compound (4) as a colorless oil. The analytical data were as follows:

Boiling point: 136°–139° C. (2 mmHg)

IR $\nu_{max}^{CHCl_3}$ cm$^{-1}$: 1745, 1605.

$^1$H-NMR (90 MHz) $\delta_{ppm}^{CDCl_3}$: 1.33 (3H, s, —CH$_3$), 1.37 (3H, s, —CH$_3$), 2.57 (1H, dd, J=15 Hz, J$_{trans}$=3 Hz, —CH$_2$CO—), 2.96 (1H, dd, J=15 Hz, J$_{cis}$=5 Hz, —CH$_2$CO—), 3.48 (1H, ddd, J=9, 5, 3 Hz, >CHN<), 3.59 (2H, m, —OCH$_2$—), 4.05 (1H, m, —OCH<), 4.19 (1H, d, J=15 Hz, —CH$_2$C$_6$H$_5$), 4.74 (1H, d, J=15 Hz, —CH$_2$C$_6$H$_5$), 7.32 (5H, s, —CH$_2$C$_6$H$_5$).

MS: m/z 262 (M+1).

[α]$_D$ −74.9° (C 0.6, benzene).

Step B [production of (4R)-1-benzyl-4-(1,2-dihydroxyethyl)-2-azetidinone]

(4) ⟶ 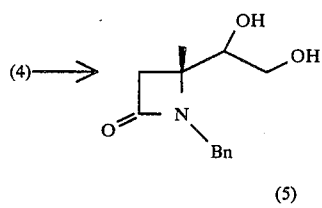

(5)

364 mg (1.4 mmoles) of the compound (4) was dissolved in 30 ml of a 4:1 mixture of acetic acid and water, and the solution was stirred at 40° C. for 14 hours. After the reaction, the solvents were evaporated under reduced pressure. The residue was subjected to thin-layer chromatography, and the resulting oily product was distilled under reduced pressure to give 245 mg (80%) of the compound (5) as a colorless oil. The analytil data were as follows:

Boiling point: 188°–192° C. (2 mmHg).
IR $\nu_{max}^{CHCl_3}$ cm$^{-1}$: 3375, 1740, 1606.
$^1$H-NMR (90 MHz) $\delta_{ppm}^{CDCl_3}$: 2.65 (1H, dd, J=13.5 Hz, J$_{trans}$=2.7 Hz, —COCH$_2$—), 2.95 (1H, dd, J=13.5 Hz, J$_{cis}$=4.5 Hz, —COCH$_2$—), 3.10 (2H, brs, —OH, vanished in D$_2$O), 3.20–3.80 (4H, m,

—CH$_2$OH), 4.32 (1H, d, J=15 Hz, —CH$_2$C$_6$H$_5$), 4.70 (1H, d, J=15 Hz, —CH$_2$C$_6$H$_5$), 7.36 (5H, s, —CH$_2$C$_6$H$_5$).
MS: m/z 222 (M+1).
[α]$_D^{19}$ −71.3° (C 0.94, EtOH).

Step C [production of (4R)-1-benzyl-4-[1,2-dimethanesulfonyloxy)ethyl]-2-azetidinone]

(5) ⟶ 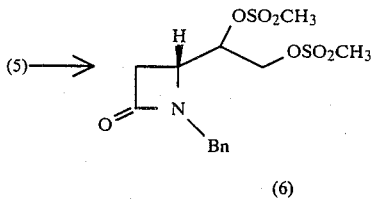

(6)

238 mg (1.1 mmoles) of the compound (5) was dissolved in 5 ml of dry dichloromethane, and 0.7 ml (5 mmoles) of triethylamine was added. Under an argon atmosphere, 0.3 ml (4 mmoles) of methanesulfonyl chloride was gradually added dropwise at 0° C., and the mixture was stirred for 1 hour. After the reaction, the solvent was evaporated under reduced pressure. The residue was subjected to thin-layer chromatography to give colorless crystals. Recrystallization of the crystals from dichloromethane gave 400 mg (quantitative) of the compound (6) as colorless needle-like crystals. The analytical data were as follows:

Melting point: 117°–119° C.
IR $\nu_{max}^{CHCl_3}$ cm$^{-1}$: 1758, 1603, 1178.
$^1$H-NMR (90 MHz) $\delta_{ppm}^{CDCl_3}$: 2.83 (1H, dd, J=15 Hz, J$_{trans}$=3 Hz, —CH$_2$CO—), 3.01 (3H, s, —SO$_2$CH$_3$), 3.07 (3H, s, —SO$_2$CH$_3$), 3.15 (1H, dd, J=15 Hz, J$_{cis}$=4.5 Hz, —CH$_2$CO—), 3.70 (1H, m, —CH<), 4.26 (1H, d, J=15 Hz, —CH$_2$C$_6$H$_5$), 4.37 (2H, m, —CH$_2$OSO$_2$CH$_3$), 4.74 (1H, d, J=15 Hz, —CH$_2$C$_6$H$_5$), 4.91 (1H, m, >CHOSO$_2$CH$_3$), 7.34 (5H, s, —CH$_2$C$_6$H$_5$).
MS: m/z 378 (M+1).
Elemental analysis: Calcd. for C$_{14}$H$_{19}$O$_7$NS$_2$: C, 44.55; H, 5.07; N, 3.71; S, 16.99, Found: C, 44.44; H, 5.09; N, 3.77; S, 16.85.
[α]$_D^{18}$ +9.2° (C 1.29, CHCl$_3$).

Step D [production of (4S)-1-benzyl-4-vinyl-2-azetidinone]

(6) ⟶ 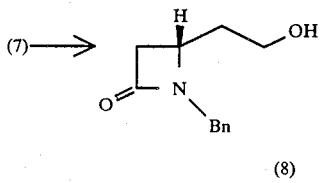

(7)

400 mg (1.1 mmoles) of the compound (6) was dissolved in 11 ml of dry DMF, and 1.6 g (11 mmoles) of sodium iodide and 0.97 g (11 mmoles) of zinc powder were added. Under an argon stream, the mixture was refluxed for 8 hours. After the reaction, the reaction mixture was diluted with diethyl ether and filtered through Celite. The solvent was evaporated from the filtrate under reduced pressure. The residue was dissolved in a 1:1 mixture of diethyl ether and dichloromethane, washed with water and a saturated aqueous solution of sodium chloride, and dried over anhydrous sodium sulfate. The solvents were evaporated, and the residue was distilled under reduced pressure to give 182 mg (92%) of the compound (7) as a pale yellow oil. The analytical data were as follows:

Boiling point: 128°–131° C. (2 mmHg).
IR $\nu_{max}^{CHCl_3}$ cm$^{-1}$: 1735, 1415.
$^1$H-NMR (90 MHz) $\nu_{ppm}^{CDCl_3}$: 2.68 (1H, dd, J=15 Hz, J$_{trans}$=3 Hz, —CH$_2$CO—), 3.16 (1H, dd, J=15 Hz, J$_{cis}$=5.5 Hz, —CH$_2$CO—), 3.88 (1H, m >CHN<), 3.98 (1H, d, J=15 Hz, —CH$_2$C$_6$H$_5$), 4.63 (1H, d, J=15 Hz, —CH$_2$C$_6$H$_5$), 5.23 (2H, m, —CH=CH$_2$), 5.74 (1H, ddd, J=18, 8, 7.5 Hz, —CH=CH$_2$), 7.29 (5H, s, —CH$_2$C$_6$H$_5$).
MS: m/z 187 (M+).
High resolution MS: C$_{12}$H$_{13}$ON; Calcd. 187.0997, Found 187.0999.
[α]$_D^{18}$: −93.6° (C 1.28, CHCl$_3$).

Step E [production of (4S)-1-benzyl-4-(2-hydroxyethyl)-2-azetidinone]

(7) ⟶

(8)

123 mg (0.6 mmole) of the compound (7) was dissolved in 6.6 mg of THF, and under an argon stream, 1.32 ml of a 1M THF solution of diborane commercially available was added, and the mixture was stirred at room temperature (20° C.) for 6 hours. Then, 6 ml of a 30% aqueous solution of hydrogen peroxide and 1.2 ml of a 3M aqueous solution of sodium hydroxide were added, and the mixture was further stirred at room temperature for 1 hour. After the reaction, the reaction mixture was dissolved in a 2:1 mixture of diethyl ether and dichloromethane, washed with a saturated aqueous solution of sodium hydrogen carbonate, water and a saturated aqueous solution of sodium chloride, and then dried over anhydrous sodium sulfate. The solvents were evaporated, and the residue was distilled under reduced pressure to give 66 mg (54%) of the compound (8) as a colorless oil. The analytical data were as follows:

Boiling point: 152°–158° C./2 mmHg.

IR $\nu_{max}^{CHCl_3}$ cm$^{-1}$: 3350, 1730, 1600.

$^1$H-NMR (90 MHz) $\delta_{ppm}^{CDCl_3}$: 1.80 (2H, m, —CH$_2$CH$_2$OH), 2.00 (1H, brs, —OH, vanished in D$_2$O), 2.66 (1H, dd, J=15 Hz, J$_{trans}$=3 Hz, —CH$_2$CO—), 3.04 (1H, dd, J=15 Hz, J$_{cis}$=5 Hz, —CH$_2$CO—), 3.61 (2H, m, —CH$_2$OH), 4.15 (1H, d, J=15 Hz, —CH$_2$C$_6$H$_5$), 4.40 (1H, m, =CHN<), 4.58 (1H, d, J=15 Hz, —CH$_2$C$_6$H$_5$), 7.30 (5H, s, —CH$_2$—C$_6$C$_5$).

MS: m/z 205 (M+).

$[\alpha]_D^{16}$ −7.6° (C 0.2, CHCl$_3$).

Step F [production of (4R)-1-benzyl-4-(methoxycarbonylmethyl)-2-azetidinone]

18.6 mg (0.09 mmole) of the compound (8) was dissolved in 0.5 ml of acetone, and three drops of the Jones reagent were added. The mixture was stirred at 0° C. for 3 hours. Then, one drop of 2-propanol was added, and the mixture was stirred for 30 minutes. After the reaction, the reaction mixture was dissolved in diethyl ether, washed with water and a staruated aqueous solution of sodium chloride, and dried over anhydrous sodium sulfate. The solvent was evaporated under reduced pressure, and the residue was dissolved in 0.3 ml of diethyl ether. A diethyl ether solution of diazomethane was added dropwise to the solution until foaming ceased. The solvent was then evaporated, and the residue was subjected to thin-layer chromatography to give 14 mg (66%) of a colorless oil (9). The analytical data were as follows:

IR $\nu_{max}^{CHCl_3}$ cm$^{-1}$: 1740.

$^1$H-NMR (90 MHz) $\delta_{ppm}^{CDCl_3}$: 2.51(2H, m, —CH$_2$CO$_2$CH$_3$), 2.70 (1H, dd, J=14 Hz, J$_{trans}$=3 Hz, —CH$_2$CO—), 3.17 (1H, dd, J=14 Hz, J$_{cis}$=5 Hz, —CH$_2$CO—), 3.60 (3H, s, —CO$_2$CH$_3$), 3.89 (1H, ddd, J=11, 6, 3 Hz, >CHN<), 4.22 (1H, d, J=15 Hz, —CH$_2$C$_6$H$_5$), 4.52 (1H, d, J=15 Hz, —CH$_2$C$_6$H$_5$), 7.32 (5H, s, —CH$_2$C$_6$H$_5$).

MS: m/z 233 (M+).

High resolution MS: C$_{13}$H$_{15}$NO$_3$; Calcd. 233.1050, Found 233.1032.

$[\alpha]_D^{17}$ −22.1° (C 0.28, benzene).

REFERENTIAL EXAMPLE 3

Production of (S)-4-(methoxycarbonylmethyl)-2-azetidinone:

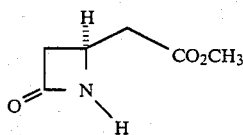

Step A [production of methyl (3R, 4S)-3-(N-benzyloxycarbonyl)-amino-4,5-O-isopropylidenepentanoate]

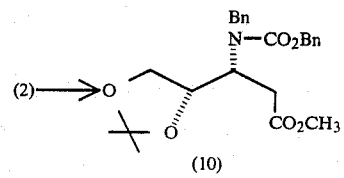

2.7 g (9.2 mmoles) of the β-amino ester (2) was dissolved in 25 ml of dry THF, and 2.8 g (20 mmoles) of potassium carbonate was added. At 0° C., 3 ml (15 mmoles) of carbobenzoxy chloride was gradually added dropwise. The mixture was stirred for 10 minutes. Then, 1.5 ml of triethylamine was added, and further a 2:1 mixture of diethyl ether and dichloromethane was added. The mixture was washed with water and a saturated aqueous solution of sodium chloride, and dried over magnesium sulfate. The solvents were evaporated under reduced pressure, and the residue was chromatographed on a silica gel column using a mixture of n-hexane, dichloromethane and acetone. Fractions containing the compound (10) were combined, and 3.8 g (94%) of the compound (10) was obtained as a colorless oil. The analytical data were as follows:

$^1$H-NMR (90 MHz) $\delta_{ppm}^{CDCl_3}$: 1.29 (3H, s, —CH$_3$), 1.36 (3H, s, —CH$_3$), 1.7 (2H, m, —CH$_2$CO—), 3.53 (3H, s, —CO$_2$CH$_3$), 4.60 (1H, d, J=16 Hz, —CH$_2$C$_6$H$_5$), 4.69 (1H, d, J=16 Hz, —CH$_2$C$_6$H$_5$), 5.21 (2H, s, —CH$_2$C$_6$H$_5$), 7.33 (10H, s, —CH$_2$C$_6$H$_5$ x2).

MS: m/z 412 (M-15).

High resolution MS: C$_{23}$H$_{26}$NO$_6$; Calcd. 412.1759 Found 412.1769.

Step B [methyl (3R, 4S)-3-(N-benzyl-N-benzyloxycarbonyl)amino-4,5-hydroxy-pentanoate]

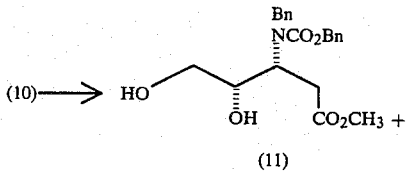

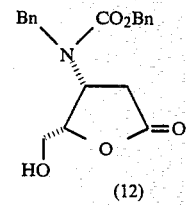

Three grams (7 mmoles) of the compound (10 was dissolved in 40 ml of a 3:1 mixture of acetic acid and water, and the solution was stirred at 40° C. for 3.5 hours. After the reaction, the solvent was evaporated under reduced pressure. The residue was chromatographed on a silica gel column using a mixture of n-hexane, dichloromethane and acetone as an eluent to give 1.85 g (71%) of the diol (11) and 452 mg (18%) of the by-product lactone (12). The analytical data were as follows:

Compound (11)

IR $\nu_{max}^{CHCl_3}$ cm$^{-1}$: 3350, 1730, 1670.

$^1$H-NMR (90 MHz) $\delta_{ppm}^{CDCl_3}$: 2.79 (2H, m, —CH$_2$CO—), 3.58 (3H, s, —CO$_2$CH$_3$), 3.76 (1H, m, >CHN<), 4.10 (1H, m, >CHOH), 4.44 (1H, d, J=16 Hz, —CH$_2$C$_6$H$_5$), 4.70 (1H, d, J=16 Hz, —CH$_2$C$_6$H$_5$), 5.23 (2H, s, —CH$_2$C$_6$H$_5$), 7.33 (5H, s, —CH$_2$C$_6$H$_5$), 7.41 (5H, s, —CH$_2$C$_6$H$_5$).

MS: m/z 387 (M+1).

$[\alpha]_D^{20}$ +22.7° (C 1.2, CHCl$_3$).

Compound (12)

Melting point: 103°–106° C.

$^1$H-NMR (90 MHz) $\delta_{ppm}^{CDCl_3}$: 2.72 (2H, m, —CH$_2$CO—), 4.50 (1H, d, J=16 Hz, —CH$_2$C$_6$H$_5$), 4.72 (1H, d, J=16 Hz, —CH$_2$C$_6$H$_5$), 5.25 (2H, s, —CH$_2$C$_6$H$_5$), 7.34 (5H, s, —CH$_2$C$_6$H$_5$), 7.42 (5H, s, —CH$_2$C$_6$H$_5$).

$[\alpha]_D^{20}$ −32.2° (C 1.4, CHCl$_3$).

Step C [production of methyl 3-(N-benzyl-N-benzyloxycarbonyl)amino-5-methoxy-4-pentenoate]

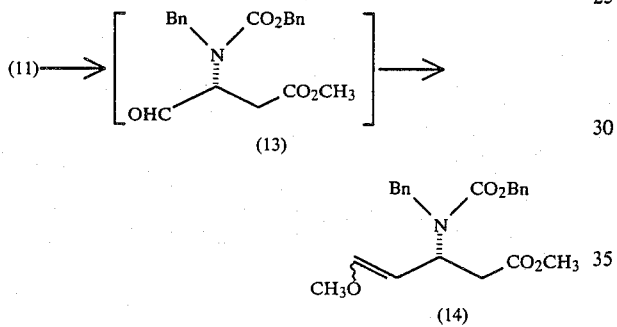

Four hundred milligrams (1 mmole) of the diol (11) was dissolved in 5 ml of dimethoxyethane, and at 0° C., 243 mg (1.1 mmoles) of sodium metaperiodate dissolved in 3 ml of water was added. The mixture was stirred for 4 hours. After the reaction, a 1:1 mixture of diethyl ether and benzene was added, and the mixture was washed with water and a saturated aqueous solution of water, and dried over magnesium sulfate. The solvents were evaporated under reduced pressure to give 365 mg (quantitative) of the aldehyde (13). Subsequently, 685 mg (2 mmoles) of a phosphonium salt Ph$_3$P$^+$CH$_2$OCH$_3$Cl$^-$ was dissolved in 10 ml of dry THF. At −10° C., 1 ml (1.5 mmoles) of n-butyl lithium (as a 1.5M n-hexane solution) was added dropwise, and the mixture was stirred for 15 minutes. A solution of 370 mg of the compound (13) in 2 ml of dry THF was added dropwise. The mixture was stirred at −10° C. for 5 minutes. After the reaction, diethyl ether and dichloromethane were added, and the reaction mixture was thus washed with a saturated aqueous solution of ammonium chloride, water and a saturated aqueous solution of sodium chloride, and dried over magnesium sulfate. The solvents were evaporated under reduced pressure. The residue was subjected to thin-layer chromatography to give 287 mg of the compound (14) as a colorless oil which was found to be a 1:1 mixture of Z-form and E-form by its $^1$H-NMR spectrum.

$^1$H-NMR (90 MHz) $\delta_{ppm}^{CDCl_3}$: 3.36 (3H, s, —CH=CHOCH$_3$), 3.50 (3H, s, —CH=CHOCH$_3$).

Step D [production of methyl (S)-3-(N-benzyl-N-benzyloxycarbonyl)amino-5,5-dimethoxypentanoate]

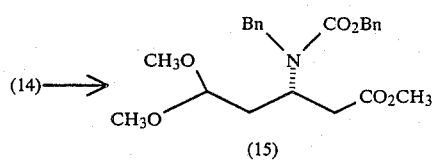

Sixty milligrams (0.16 mmole) of the compound (14) was dissolved in 2 ml of methanol, and 15 mg (0.06 mmole) of CSA was added. The mixture was stirred at room temperature (20° C.) for 12 hours. After the reaction, a saturated aqueous solution of sodium hydrogen carbonate was added to the reaction mixture, and a mixture of diethyl ether and dichloromethane was also added. The mixture was washed with water and a saturated aqueous solution of sodium chloride, and dried over magnesium sulfate. The solvents were evaporated under reduced pressure. The residue was subjected to thin-layer choromatography to give 55 mg (85%) of the title compound (15) as a colorless oil. The analytical data were as follows:

IR $\nu_{max}^{CHCl_3}$ cm$^{-1}$: 1730, 1690.

$^1$H-NMR (90 MHz) $\delta_{ppm}^{CDCl_3}$: 1.93 (2H, m, —CH$_2$CHN<), 2.67 (2H, m, —CH$_2$CO—), 3.12 (3H, s, —OCH$_3$), 3.18 (3H, s, —OCH$_3$), 3.53 (3H, s, —CO$_2$CH$_3$), 4.18 (1H, t, —CH(OCH$_3$)$_2$), 4.50 (2H, s, —CH$_2$C$_6$H$_5$), 5.20 (2H, s, —CH$_2$C$_6$H$_5$), 7.28 (5H, s, —CH$_2$C$_6$H$_5$), 7.34 (5H, s, —CH$_2$C$_6$H$_5$).

MS: m/z 400 (M-15).

$[\alpha]^{20}$ +8.3 (C 1.2, CHCl$_3$).

Step E [production of methyl (S)-3-(N-benzyl-N-benzyloxycarbonyl)amino-4-formylbutanoate]

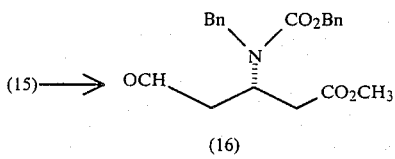

56 mg (0.13 mmole) of the compound (15) was dissolved in 1.6 ml of a 3:1 mixture of acetic acid and water, and the solution was stirred at room temperature for 10 hours and then at 40° C. for 1.5 hours. The solvents were evaporated under reduced pressure. The residue was subjected to thin-layer chromatography to give 49 mg (quantitative) of the compound (16) as a colorless oil. The analytical data were as follows:

Step F [production of methyl (S)-3-(N-benzyl-N-benzyloxycarbonyl)amino-4-carboxybutanoate]

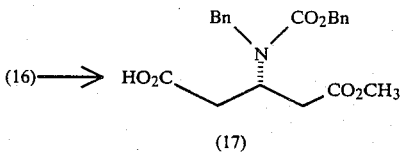

49 mg (0.13) mmole) of the compound (16) was dissolved in 1.5 ml of acetone, and three drops of the Jones reagent were added. At 0° C., the mixture was stirred for 5 minutes. Then, one drop of 2-propanol was added, and at 0° C., the mixture was stirred for 5 minutes. After the reaction, a 2:1 mixture of diethyl ether and dichloromethane was added, and the mixture was washed with water and a saturated aqueous solution of sodium chloride, and dried over magnesium sulfate. The solvents were evaporated under reduced pressure to give 51 mg of the title compound (17) in a quantitative yield. The analytical data were as follows:

IR $\nu_{max}^{CHCl_3}$ cm$^{-1}$: 2725, 1725, 1690.

$^1$H-NMR (90 MHz) $\delta_{ppm}^{CDCl_3}$: 3.61 (3H, s, —CO$_2$CH$_3$), 4.48 (1H, d, J=16 Hz, —CH$_2$C$_6$H$_5$), 4.71 (1H, d, J=16 Hz, —CH$_2$C$_6$H$_5$), 5.24 (2H, s, —CH$_2$C$_6$H$_5$), 7.36 (5H, s, —CH$_2$C$_6$H$_5$), 7.43 (5H, s, —CH$_2$C$_6$H$_5$), 9.66 (1H, brs. —CHO).

Step G [production of (S)-4-(methoxycarbonylmethyl)-2-azetidinone]

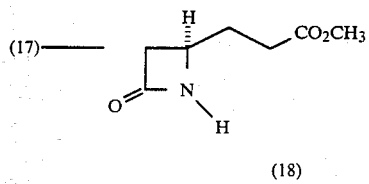

55 mg (0.15 mmole) of the compound (17) was dissolved in 2 ml of methanol, and 10 mg of 10% palladium-activated carbon was added. Under a hydrogen stream, the mixture was stirred at room temperature (20° C.) for 15 hours, and then at 50° C. for 2 hours. After the reaction, the palladium-activated carbon was removed by using Celite. The solvent was removed from the filtrate under reduced pressure to give 20 mg of β-amino acid. Subsequently, the β-amino acid was dissolved in 8 ml of acetonitrile, and 23 mg (0.089 mmole) of triphenylphosphine and 20 mg (0.089 mmole) of pyridine disulfide were added. The mixture was refluxed for 12 hours. After the reaction, the reaction mixture was diluted with diethyl ether, and filtered on Celite. Then, the solvent was evaporated under reduced pressure. The residue was subjected to thin-layer chromatography to give 14 mg (80%) of the title compound (18). The analytical data were as follows:

IR $\nu_{max}^{CHCl_3}$ cm$^{-1}$: 1755, 1730.

$^1$H-NMR (90 MHz) $\delta_{ppm}^{CDCl_3}$: 2.65 (3H, m), 3.18 (1H, ddd, J=13, 6.3 Hz, —CH$_2$CO—), 3.72 (3H, s, —CO$_2$CH$_3$), 3.92 (1H, m, >CHN<).

MS: m/z 143 (M+).

$[\alpha]_D^{20}$+64.5 (C 0.2, CHCl$_3$).

What is claimed is:

1. A compound represented by the formula

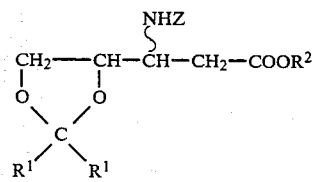

wherein R$^1$ represents a lower alkyl group, a phenyl group or a benzyl group, or the two R$^1$ groups together represent a group of the formula —CH$_2$—$_n$ in which n is an integer of 4 to 7; R$^2$ represents a hydrogen atom, an alkyl group, or a substituted or unsubstituted aralkyl group; and Z represents a hydrogen atom, a lower alkyl group or a substituted or unsubstituted benzyl group.

2. A compound according to claim 1 which is represented by the following formula

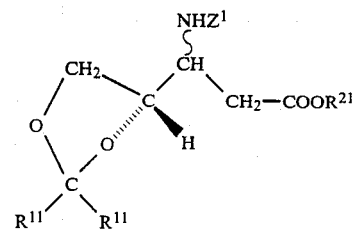

wherein R$^{11}$ represents a methyl or ethyl group or the two R$^{11}$ groups together represent —CH$_2$—$_5$; R$^{21}$ represents a hydrogen atom or a lower alkyl group; and Z$^1$ represents a group of the formula

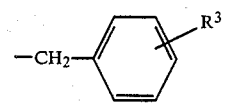

in which R$^3$ represents a lower alkyl group or a lower alkoxy group.

3. The compound of claim 1 which is represented by the following formula

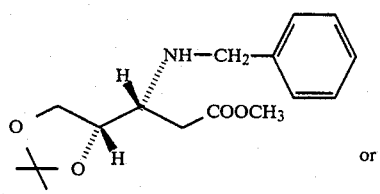

or

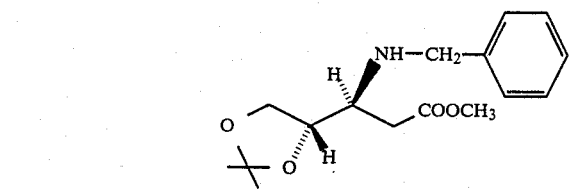

4. A process for producing a compound represented by the formula

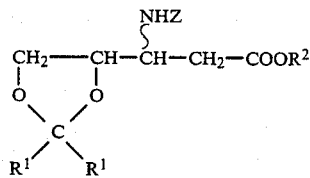

wherein R$^1$ represents a lower alkyl group, a phenyl group or a benzyl group, or the two R$^1$ groups together represent a group of the formula —CH$_2$—$_n$ in which n is an integer of 4 to 7; R$^2$ represents a hydrogen atom, an alkyl group, or a substituted or unsubstituted aralkyl group; and Z represents a hydrogen atom, a lower alkyl group or a substituted or unsubstituted benzyl group, which comprises subjecting a compound represented by the following formula $$CH_2-CH-CH=CH-COOR^2 \quad (II)$$

with the $O$ and $O$ connected to $C$ bearing $R^1$ and $R^1$ wherein $R^1$ and $R^2$ are as defined above, and an amine represented by the following formula $$ZNH_2 \quad (III)$$

wherein Z is as defined above, to the Michael's addition reaction.

* * * * *